United States Patent [19]

Opitz et al.

[11] Patent Number: 4,918,076
[45] Date of Patent: Apr. 17, 1990

[54] TREATING ALCOHOL ADDICTION WITH 1,4-DIHYDROPYRIDINE DERIVATIVES

[75] Inventors: Klaus Opitz, Muenster; Jörg Traber, Lohmar, both of Fed. Rep. of Germany

[73] Assignee: Troponwerke GmbH & Co. KG., Cologne, Fed. Rep. of Germany

[21] Appl. No.: 314,345

[22] Filed: Feb. 22, 1989

[30] Foreign Application Priority Data

Feb. 27, 1988 [DE] Fed. Rep. of Germany ....... 3806277

[51] Int. Cl.⁴ .......................................... A61K 31/435
[52] U.S. Cl. ................................................... 514/277
[58] Field of Search ......................................... 514/277

[56] References Cited

PUBLICATIONS

Chem. Abst. (Little), 106-45573n (1987).

*Primary Examiner*—Stanley J. Friedman
*Attorney, Agent, or Firm*—Sprung Horn Kramer & Woods

[57] ABSTRACT

A method of treating a patient afflicted with alcohol addiction which comprises administering to such patient an amount effective therefor of a dihydropyridine of the formula

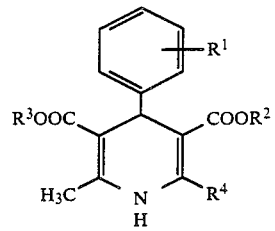

in which $R^1$ is one or two substituents independently selected from the group consisting of nitro, halogen, trifluoromethyl and $OCHF_2$, $R^2$ and $R^3$ each independently is alkyl with 1 to 12 carbon atoms optionally substituted by alkoxy with 1 to 4 C atoms, hydroxyl, halogen or N-methyl-N-benzylamino, and $R^4$ is cyano or alkyl with 1 to 4 carbon atoms optionally substituted by hydroxyl or halogen.

10 Claims, No Drawings

TREATING ALCOHOL ADDICTION WITH 1,4-DIHYDROPYRIDINE DERIVATIVES

The invention relates to the use of 1,4-dihydropyridine derivatives for the preparation of medicaments for the treatment of alcohol addiction and corresponding medicaments.

Dihydropyridines with a calcium-antagonistic action are known (British Patent 1,173,862, British Patent 1,358,951, U.S. Pat. No. 4,256,749 and U.S. Pat. No. 4,264,611). A number of pharmacological actions, such as, for example, a coronary action, action on the blood pressure, diuretic action or antiischaemic action in the cerebral region, have already been described for these dihydropyridines.

It is known from Life Sciences 39, 2059 to 2065 (1986) that in alcohol-dependent rats which are treated with the 1,4-dihydropyridines nitrendipine and nimodipine, the occurrence of withdrawal symptoms can be largely prevented. Withdrawal symptoms manifest themselves in alcoholics by nausea, vomiting, diarrhoea, attacks of cramp, sleeplessness and deliria (Roche Lexikon, Medizin, 8 (1984)).

The use of dihydropyridines of the general formula (I)

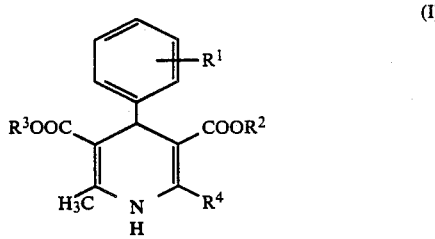

in which
R$^1$ stands for one or two identical or different substituents from the group comprising nitro, halogen, trifluoromethyl or OCHF$_2$,
R$_2$ and R$^3$ are identical or different and each stands for alkyl with 1 to 12 carbon atoms, which is optionally substituted by alkoxy with 1 to 4 C atoms, hydroxyl, halogen or N-methyl-N-benzylamino and
R$^4$ stands for cyano or alkyl with 1 to 4 carbon atoms, which is optionally substituted by hydroxyl or halogen,
has been found for the preparation of medicaments for the treatment of alcohol addiction.

Alcohol addiction (craving) is understood as compulsive dependence on alcohol consumption. The alcoholic recognizes the consequences of his behavior or continues alcohol consumption in spite of insight (inability to abstain).

Surprisingly, treatment with the 1,4-dihydropyridine according to the invention leads to a lasting elimination of the addiction symptoms.

In the context of the formula (I), the substituents in general have the following meaning:

Halogen can stand for fluorine, chlorine, bromine and iodine, in particular for fluorine and chlorine.

Alkyl (R$^2$ and R$^3$) can be a straight-chain or branched hydrocarbon radical with 1 to 12, preferably 1 to 6, carbon atoms. Methyl, ethyl, propyl, iso-propyl, butyl, iso-butyl, pentyl, iso-pentyl, hexyl and iso-hexyl are preferred.

The hydrocarbon radical in the alkyl or alkoxy groups preferably contains 1 to 4 carbon atoms. Preferred alkyl groups which may be mentioned are methyl, ethyl, propyl, iso-propyl, butyl and iso-butyl, and preferred alkoxy groups which may be mentioned are methoxy, ethoxy, propoxy, iso-propoxy, butoxy and iso-butoxy.

1,4-Dihydropyridines from the group comprising nifedipine, niludipine, nisoldipine, nitrendipine, nimodipine, felocipine and nicardipine are of particular importance.

Corresponding medicaments according to the invention are characterized in that they contain 1,4-dihydropyridine derivatives of the formula (I).

The preparation of the 1,4-dihydropyridine derivatives is known per se and can be carried out, for example, by reaction of corresponding ylidene derivatives with enamines (DE-A 3,312,283).

The medicaments according to the invention in general contain 1 to 15% by weight, preferably 5 to 10% by weight, of 1,4-dihydropyridine derivatives based on the formulation.

It is of course possible for the medicaments according to the invention to contain further active compounds which are known per se.

The medicaments according to the invention can be converted in a known manner into the customary formulations, such as tablets, coated tablets, pills, granules, aerosols, syrups, emulsions, suspensions and solutions, using inert non-toxic pharmaceutically suitable excipients or solvents.

The formulations are prepared, for example, by extending the active compounds with solvents and/or excipients, if appropriate using emulsifying agents and/or dispersing agents, and, for example, in the case of the use of water as the diluent organic solvents can be used as auxiliary solvents if appropriate.

Examples of auxiliaries which may be mentioned are: water, non-toxic organic solvents, such as paraffins (for example petroleum fractions), vegetable oils (for example groundnut/sesame oil) and alcohols (for example ethyl alcohol and glycerol), excipients such as, for example, natural rock powders (for example kaolins, aluminas, talc and chalk), synthetic rock powders (for example highly disperse silicic acid and silicates), sugars (for example sucrose, lactose and glucose), emulsifying agents (for example polyoxyethylene fatty acid esters, polyoxyethylene fatty alcohol ethers, alkylsulphonates and arylsulphonates), dispersing agents (for example lignin-sulphite waste liquors, methylcellulose, starch and polyvinylpyrrolidone) and lubricants (for example magnesium stearate, talc, stearic acid and sodium lauryl sulphate).

Administration is effected in the customary manner, preferably orally, parenterally, perlingually or intravenously. In the case of oral use, tablets can of course also contain, in addition to the excipients mentioned, additives such as sodium citrate, calcium carbonate and dicalcium phosphate, together with various additional substances, such as starch, preferably potato starch, gelatine and the like. Lubricants, such as magnesium stearate, sodium lauryl sulphate and talc, can moreover also be used for tablet-making. In the case of aqueous suspensions, various favor correctants or dyestuffs can be added to the active compounds in addition to the abovementioned auxiliaries.

For parenteral use, solutions of the active compounds can be employed, using suitable liquid excipients. In general, it has proved advantageous to administer amounts of about 0.01 to 0.5 mg/kg of body weight to achieve effective results in the case of intravenous administration, and in the case of oral administration the dosage is about 0.01 to 20 mg/kg, preferably 0.1 to 10 mg/kg, of body weight.

Nevertheless, it may be necessary, if appropriate, to deviate from the amounts mentioned, and in particular as a function of the body weight or the nature of the mode of administration, the individual behavior towards the medicament, the nature of its formulation and the time or interval at which administration takes place. Thus it can in some cases be sufficient to manage with less than the abovementioned minimum amount, whereas in other cases the upper limit mentioned must be exceeded. Where larger amounts are administered, it may be advisable to divide these into several individual doses over the course of the day.

No satisfactory agent is known for medicamentous treatment of alcohol addiction. The enzyme inhibitors disulfiram and nitrefazole cause an unpleasant reaction when the alcoholic treated with these drinks alcohol, so that he discontinues the alcohol in spite of an existing desire.

In contrast to these substances, the 1,4-dihydropyridines according to the invention inhibit, according to the invention, the voluntary consumption of alcohol by alcohol-dependent persons. In particular, the use of 1,4-dihydropyridine derivatives can prevent relapse.

EXAMPLE

Determination of the activity

Ethanol-preferent rats are housed individually in large cages under standardized conditions (12 hour light-dark rhythm, 23±1° C.). Breeding food, drinking water and 10% by volume ethanol are available to the animals in unlimited amounts, but only during the dark phase from 20.00 to 08.00 hours. The substances under investigation or the solvent (2 ml of Cremophor ® EL, 0.3 ml of 1,2-propanediol, distilled water to 10 ml) are administered once orally (2 ml/kg, stomach tube), and in particular 30 to 20 minutes before the start of the dark phase. The food vessels and the drinking bottles are weighed every morning and the amounts consumed are determined. The amount of alcohol drunk (10% by volume) in percent of the total liquid intake is a measure of the preference. The consumptions measured after the administration of a test substance are compared with the average consumptions on the three preceding days (preperiod). The particular change in the total liquid intake and the change in the gram/kg of body weight of absolute alcohol consumption measured as a percentage of the average values determined during the appropriate three-day pre-period are shown in Table 1. Statistical calculations are performed by the student t-test for paired values.

TABLE 1

| Ingestive behavior of eight male ethanol-preferent rats | | |
|---|---|---|
| Nimodipine dose (mg/kg p.o.) | Change in total liquid intake (%) | Change in absolute alcohol consumption (%) |
| 0 (solvent) | +6.9 ns | +8.4 ns |
| 5 | +1.7 ns | −26.2* |
| 10 | −1.8 ns | −44.0** |

*p < 0.05
**p < 0.001
ns not significant

The data show a marked and highly significant decrease in absolute alcohol consumption for nimodipine. The preference of the rats for alcohol accordingly decreases greatly after administration of nimodipine. The total liquid intake is not changed significantly.

If desired, the instant active materials can be administered in the form of physiologically acceptable salts.

It will be appreciated that the instant specification and claims are set forth by way of illustration and not limitation, and that various modifications and change may be made without departing from the spirit and scope of the present invention.

What is claimed is:

1. A method of treating the alcohol craving of a patient afflicted with alcohol addiction which comprises administering to such patient an amount effective therefor of a dihydropyridine of the formula

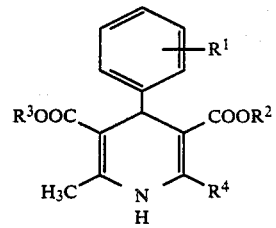

in which
R¹ is one or two substituents independently selected from the group consisting of nitro, halogen, trifluoromethyl and OCHF₂,
R² and R³ each independently is alkyl with 1 to 12 carbon atoms optionally substituted by alkoxy with 1 to 4 C atoms, hydroxyl, halogen or N-methyl-N-benzylamino, and
R⁴ is cyano or alkyl with 1 to 4 carbon atoms optionally substituted by hydroxyl or halogen.

2. The method according to claim 1, wherein the dihydropyridine is selected from the group consisting of nifedipine, niludipine, nisoldipine, nitrendipine, nimodipine, felodipine and nicardipine.

3. The method according to claim 1, wherein the dihydropyridine is administered as a composition in which it is present in about 1 to 15% by weight.

4. The method according to claim 1, wherein the dihydropyridine is nifedipine.

5. The method according to claim 1, wherein the dihydropyridine is niludipene.

6. The method according to claim 1, wherein the dihydropyridine is nisoldipine.

7. The method according to claim 1, wherein the dihydropyridine is nitrendipine.

8. The method according to claim 1, wherein the dihydropyridine is nimodipine.

9. The method according to claim 1, wherein the dihydropyridine is felodipine.

10. The method according to claim 1, wherein the dihydropyridine is nicardipine.

* * * * *